US006472166B1

(12) United States Patent
Wardlaw et al.

(10) Patent No.: US 6,472,166 B1
(45) Date of Patent: *Oct. 29, 2002

(54) METHOD FOR DETERMINING THE EFFECTS OF A GROWTH-ALTERING AGENT ON A MICROBIAL COLONY

(75) Inventors: Stephen C. Wardlaw, Lyme; Robert A. Levine, Guilford, both of CT (US)

(73) Assignee: Wardlaw Partners LP, Lyme, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/506,157

(22) Filed: Feb. 17, 2000

(51) Int. Cl.[7] .............................. C12Q 1/18; C12Q 1/00
(52) U.S. Cl. ............................................. 435/32; 435/4
(58) Field of Search ........................................ 435/32, 4

(56) References Cited

U.S. PATENT DOCUMENTS

| 4,054,490 A | 10/1977 | Vesterbera .................... 435/32 |
| 4,204,045 A | 5/1980 | Kiellander et al. ........... 435/32 |
| 4,514,495 A | 4/1985 | Schalkowskv et al. ........ 435/32 |
| 4,720,463 A | 1/1988 | Farber et al. ................ 435/291 |
| 4,724,215 A | 2/1988 | Farber et al. ................ 435/291 |
| 4,778,758 A | 10/1988 | Ericsson et al. .............. 435/32 |
| 4,856,073 A | 8/1989 | Farber et al. ................... 382/6 |
| 5,164,301 A | 11/1992 | Thompson ................... 435/32 |
| 5,206,151 A | 4/1993 | Robertson .................... 435/32 |
| 5,246,837 A | 9/1993 | Schalkowski ................ 435/32 |
| 5,501,959 A | 3/1996 | Lancaster et al. ............. 435/32 |
| 5,563,043 A | 10/1996 | Schalkowski et al. ........ 435/32 |
| 5,639,632 A | 6/1997 | Ericsson et al. .............. 435/32 |
| 5,922,282 A | 7/1999 | Ledley ......................... 422/50 |
| 6,022,734 A | * 2/2000 | Wardlaw ................. 435/288.7 |
| 6,153,400 A | * 11/2000 | Matsumura et al. .......... 435/32 |
| 6,284,526 B1 | * 9/2001 | Wardlaw ................. 435/288.7 |

FOREIGN PATENT DOCUMENTS

EP    0 635 126 B1    7/1999    .......... G01N/15/14

OTHER PUBLICATIONS

Medical Microbiology, "An Introduction to Infectious Diseases", Second Edition, John C. Sherris, Editor, pp. 38–41.
Sherris, John C., "Medical Microbiology: An Introduction to Infectious Diseases", Second Edition (1990) by Elsevier Science Publishing Co., Inc.

* cited by examiner

Primary Examiner—Louise N. Leary
(74) Attorney, Agent, or Firm—McCormick, Paulding & Huber LLP

(57) ABSTRACT

A method for determining the effects of a growth-altering agent on one or more microbial colonies is provided. The method utilizes a growth-altering agent incorporated into at least a portion of a growth medium, and includes the steps of: (a) incubating the colony-forming units in a manner likely to cause the colony-forming units to replicate into microbial colonies; (b) inoculating the growth medium with an inoculum having one or more viable colony-forming units; (c) quantifying one or more characteristics of one or more individual microbial colonies exposed to the growth-altering agent; and (d) evaluating the quantified characteristics to determine the effects of the growth-altering agent on the individual microbial colonies.

37 Claims, 4 Drawing Sheets

METHOD FOR DETERMINING THE EFFECTS OF A GROWTH-ALTERING AGENT ON A MICROBIAL COLONY

BACKGROUND OF THE INVENTION

1. Technical Field

The present invention relates to methods for determining the effects of a growth-altering agent on one or more microorganisms within a biological sample in general, and to methods for determining the effects of a growth-altering agent on individual microorganism colonies within a biological sample in particular.

2. Background Information

Effective patient treatment often requires an identification of microorganisms within a biological sample and a determination of the sensitivity of those microorganisms to growth-altering agents. Historically, biological samples have been taken and applied to or added to microbiologic growth media (called "cultures"), which were then examined and tested primarily on a macroscopic basis. In most conventional tests, a suitable growth medium is inoculated with a patient's sample and subsequently incubated until there is visible evidence of microorganism growth. Most organisms require an incubation period of at least 18 to 24 hours to form visible colonies. The individual colonies start as a single, or a small cluster of microscopic cells or viable units (collectively referred to as colony-forming units or CFU's) contained within the inoculum. After an initial lag period during which time the organism acclimates itself to its new environment and experiences little or no growth, the viable microorganisms settle into exponential growth: one cell will give rise to two cells in one generation, eight cells in three generations, sixty-four cells in six generation, and so forth until a visible colony is created.

If the inoculum contains a plurality of different microorganisms, each organism type will form its own characteristic colony, which may or may not be distinguishable from another. For most purposes, however, it is desirable to have only a single species of organism present within the organism growth. For example, if one wishes to test a biological sample for sensitivity to a particular antibiotic and the sample and subsequent culture contain multiple organism species, it may not be possible to determine the sensitivity of individual organism species within the culture to the antibiotic. To determine the sensitivity of individual organism species, it is necessary to make a "pure" culture (i.e., one that contains a single species of microorganism) by incubating the initial sample inoculum on a first solid growth medium and removing a single colony, or a group of identical colonies, from a first growth medium and plating it onto a second solid growth medium or forming a suspension if a liquid culture is used. A person of skill in the art will recognize the process is time consuming and generally requires a skilled technician.

In those instances where it is desirable to know the effectiveness of a growth-altering agent (e.g., antibiotics, growth promoting agents, nutrients, antiseptics, etc.) on an organism, prior art practice generally dictates the use of one of the following evaluative methods. In one method, a growth-altering agent is applied to a region of a solid inoculated growth medium prior to incubation and the organism growth in the applied region is evaluated or compared against organism growth in a region where growth-altering agent was not applied. A Kirby-Bauer plate test is an example of this type of macroscopic method. The Kirby-Bauer method includes incubating a growth medium until confluent growth forms over the growth medium. A region of growth medium bearing an effective growth-altering agent (antimicrobial) diffused out from a disk will not contain organism growth if the antimicrobial is effective in suppressing the organism. The size of the growth-free zone surrounding the disk is then compared to a reference to determine whether the organism is susceptible to the growth-altering agent in a clinically useful concentration. A second evaluative method involves adding a known amount of the growth-altering agent to a liquid medium that is inoculated with the organism to be tested. Turbidity testing is an example of this type of macroscopic method. A turbidity test measures the "cloudiness" of a liquid sample to determine the organism content of the sample. An increase in the turbidity of the sample indicates an increase in the organism content within the sample. A third evaluative method involves observing the effect organism growth has on a colored reagent that responds to one or more constituents or metabolic products of the growing organism. The information available from any of these macroscopic evaluation methods is, generally speaking, also macroscopic in nature; e.g., the growth-altering agent applied in a particular concentration either has or does not have an effect on the growth of the organism(s). Little or no additional information is available regarding, for example, the mechanism of death, whether the organism experienced septum formation, or any statistical information vis-a-vis the population of organisms within the culture.

One of the problems with the above macroscopic methods is test error that results from waiting until a visible layer or an acceptable concentration of organism develops. Organism colonies growing on or within a growth medium compete for food and as a result may be growth inhibited because of competition rather than because of a growth-altering agent. Those same organisms can also affect each other by their excretions and metabolic by-products. A more accurate analysis of the effect of a growth-altering agent on a particular microbe would be possible if such interference did not occur.

Another problem with macroscopic evaluation of an organism is the time required to produce meaningful results. As noted above, it is typically necessary to incubate an organism culture anywhere from 18 to 24 hours to produce a growth adequate for macroscopic evaluation (e.g., if the organism replicates every 20 to 60 minutes, there should be at least 20 generations of the organism). Practically speaking, however, generating a culture and analyzing it using conventional methods takes at least 48 hours because of handling, evaluation, etc. Because the rate of microbial growth is so rapid and the time for testing so great, patients suspected of having a microbial infection are often initially treated with a wide-spectrum antibiotic prior to the identification of the actual organism and its sensitivity. A more targeted treatment can be administered after the test data is received. A person of skill in the art will recognize, however, that wide spectrum antibiotics having the utility to provide more expeditious treatment are not favored over the more targeted treatments available with specific information. In fact, a wide spectrum antibiotic can be considerably more expensive and have more adverse side effects than a more targeted drug. There is also considerable concern today that the overuse of wide spectrum antibiotics might promote the development of antibiotic resistance within the organisms, consequently limiting their effectiveness.

In recognition of the problems associated with the time it takes to perform the above described macroscopic tests, a number of methods for rapidly determining antibiotic susceptibility have been proposed, including methods that examine individual organisms. These methods utilize the fact that susceptible bacteria may change their shape, size, or internal chemistry (or some combination thereof) when exposed to an antibiotic Some types of bacteria, however, do not detectably react to an antibiotic until after the propagation of the first few generations. Tests that only consider organisms in their first few generations, therefore, cannot provide useful information in every case and are considered to be ineffective unless the behavior of the organism is known in advance. An example of an analysis for a specific microorganism is proposed by Ledley (U.S. Pat. No. 5,922, 282) for the determination of antibiotic susceptibility for mycobacterium tuberculosis (MTB). In the Ledley method, the DNA of individual organisms are altered by the addition of a plasmid which will cause the living organisms to fluoresce. The fluorescence of the organisms is compared before and after the addition of an antimicrobial agent to determine if the agent has extinguished the fluorescence and therefore killed the MTB organisms. This single-organism technique is similar to those previously published except for the means of creating fluorescence, and is only applicable to a narrow range of organisms. Another method for determining the effects of a growth-altering agent in a liquid broth is described in European Patent Specification No. EP 0 635 126 B1. In the European Patent Specification, image processing is used to determine changes in size, number, or shape of individual organisms to determine if there are effects from an antibiotic. A problem with this approach is that because it is performed in a liquid medium, we believe it to be impossible to analyze effects on a specific CFU or characteristics of that CFU's such as the CFU's replication rate.

Other methods for monitoring microbial growth and metabolism have been proposed that add agents designed to change color when exposed to microbial growth. Still other methods (as disclosed in U.S. Pat. Nos. 4,724,215; 4,720, 463; and 4,856,073) examine microbial changes with a video camera. To the best of our knowledge, all of these methods are macroscopic in nature and consequently do not provide information about individual microbial colonies in their earliest stages and thus cannot provide reliable antibiotic resistance information in a very short period of time. They can provide only macroscopic information; i.e., whether or not the growth-altering agent had a detectable effect on the microbial growth.

It is also well known that all bacteria within-a given respond in the same manner to any particular growth-altering agent. There is a variation of resistance to growth-altering agents within any microbial population that is not easily quantified using any current technique. If this population data were routinely available, it may be possible to predict the likelihood of developing antibiotic resistance for the microbe in question and thus help determine the optimum length of treatment.

All previous methods of examining the effects of growth-altering agents on microorganisms of which we are aware can be grouped into two basic categories. The first group looks at the effects of organism growth visible to the naked, unaided eye; e.g., the formation of a visible colony or turbidity, or a color change associated with such growth. The second group relies on changes within single organisms within a liquid growth medium prior to logarithmic growth.

What is needed is a method for determining the reaction of a microbe to a growth altering agent, one that enables the microbe to be identified, one that can provide the aforementioned information in a fraction of the time it currently takes commercially available methods to provide it, and one that does not require visible macroscopic growth nor is limited to looking at single organisms.

DISCLOSURE OF THE INVENTION

It is, therefore, an object of the present invention is to provide a method for investigating the effects of growth-altering agents on microbial colonies within the first few hours of incubation.

It is another object of this invention to provide a method for identifying a microorganism by determining which nutrients or inhibitors affect its growth.

The present invention provides a method for determining the effects of a growth-altering agent on a microbial colony. The terms "microbial colony" or "microcolony", as used herein refer to a microbial colony in its earliest stages of development, prior to its becoming readily visible to the naked eye. As used herein, the term "growth-altering agent" includes agents that will alter, inhibit, or enhance microbial growth. Examples of growth-altering agents include, but are not limited to antibiotics, antiseptics, nutrients, or growth promoting agents. Growth-altering agents can also be environmental type agents such as temperature, humidity, light, gaseous environment.

Each microbial colony analyzed under the present method is an individual microscopic colony that forms from a colony-forming unit (CFU) present within an inoculum. Meaningful information can be produced under the present method using colonies in a growth range that includes colonies that have doubled once from their CFU to those that have doubled twenty or so [fewer] times. The growth range of colonies capable of providing meaningful information under the present method may also be described in terms of growth time, colony size, or progeny. In most cases, the microbial colonies utilized under the present method generally cannot be seen by the naked human eye. Hence, the present method can be described as microscopic in contrast to prior art methods that macroscopically evaluate multiple microbial colonies contiguous with one another that are collectively large enough so as to be viewable by the naked eye. In addition, the present method reliably quantitates the growth characteristics.

The present method utilizes a solid or semi-solid growth medium and a growth-altering agent incorporated in at least a portion of the growth medium, and includes the following steps:

(a) inoculating the growth medium with an inoculum having one or more viable colony-forming units;

(b) incubating the colony-forming units in a manner likely to cause the colony-forming units to replicate into microbial colonies;

(c) quantifying one or more characteristics of one or more individual microbial colonies exposed to the growth-altering agent; and (d) evaluating the quantified characteristics to determine the effects of the growth-altering agent on the individual microbial colonies.

During the quantifying step, characteristics of microbial colonies exposed to a growth-altering agent and in some instances characteristics of microbial colonies located in a control reference are quantified. A colony characteristic can be anything that can be quantified to provide meaningful data regarding the effects of the growth-altering agent on the colony. Colony characteristics typically useful for determining effects include, but are not limited to, colony area, perimeter, perimeter-to-area ratio, edge roughness, edge contour, and uniformity of colony density. The process used to quantify a characteristic can be varied to suit the determination at hand, the characteristic being quantified, and the level of specificity necessary to provide useful data. Quantifying processes include, but are not limited to, measurement, comparative, and inspection type processes. Quantifying is performed as a function of time. In all cases, the characteristics are quantified to ascertain change. In most cases, change is determined by comparing characteristics at two or more points in time (e.g., at $T_1, T_2, T_3, \ldots, T_N$). In some cases, however, it may be possible to acquire meaningful information by quantifying a characteristic(s) at a single point in time. The number of times a microbial colony or colonies must be quantified will depend on the sufficiency of data collected; i.e., whatever number of times is necessary to make a clinically sufficient determination regarding the effects of the growth-altering agent. The mechanism used during the quantifying step is typically an imaging device (e.g., a digital camera, etc.) that produces an image with a clarity that is sufficient to allow the characteristics captured within the image to be measured, compared, inspected, or otherwise quantified. Other imaging devices such as bar scanners or flying-spot scanners may be used alternatively. Microcolony images can be utilized in real-time and/or saved.

The determination of the effects of the growth-altering agent on a microbial colony is made by evaluating the quantified characteristics. The manner in which the quantified characteristic is evaluated will, like the quantifying step, depend on determination at hand, the characteristic being quantified, and the level of specificity necessary to provide useful data. In some instances, the evaluation may only look at whether a quantified characteristic is present (e.g., whether colony growth exists, or whether the edge of a colony is rough, etc.) and that evaluation may take place using the characteristic data collected at a single point in time, or at a plurality of points in time. The determination of the effects the growth-altering agent has on the microbial colony in such cases, may be made based on the quantified characteristic alone. In other instances, the determination can be made by evaluating the quantified characteristic in view of a control reference.

A control reference may be any source of information that provides data useful in evaluating the characteristic of the microbial colony being considered. For example, if the inoculum contains a known organism, the evaluation could be performed using a control reference that provides data relating normal growth characteristics for that organism under similar environmental conditions; e.g., clinically developed data, etc. Alternatively, the evaluation can be performed using a control reference in the form of a section of growth medium inoculated with the same inoculum and incubated under similar conditions that is either not subjected to the growth-altering agent at all or is subjected to a different concentration of growth-altering agent. The characteristics of a colony in the control reference portion of the growth medium and the characteristics of a colony in the growth-altering agent applied region of the growth medium are quantified and evaluated in view of one another. In many instances, a comparative evaluation will yield data sufficient to make the determination. Other types of evaluation may be used alternatively.

The present method provides several significant advantages over the methods presently available for determining the sensitivity of an organism to a particular growth-altering agent. One distinct advantage is the speed by which a determination can be made regarding the effects of a growth-altering agent on an organism. This is particularly true when the present method is used to determine the effect that an antibiotic has on one or more organisms. As stated above, wide-spectrum antibiotics are often administered because of the initial lack of specific information from the patient's sample. Wide-spectrum antibiotics are not favored over narrowly focused antibiotics because they can expose the patient to greater risk of adverse side effects, their overuse might promote the development of antibiotic resistance within the organisms, and they can also be very expensive. Using the present method, antibiotic sensitivity information can quite often be provided in two hours or less which is dramatically less than the typical turnaround possible using currently available methods. As a result, it is now often possible to effectively use narrowly focused antibiotics from the start, rather than initially treating the patient with a wide-spectrum antibiotic.

Several advantages stem from the fact that the present method determines the effects of a growth-altering agent on an organism using characteristic data collected from individual colonies. As stated above, the present method utilizes colonies very early in the incubation process (colonies that have doubled generally between two and twenty times) prior to any macroscopic aggregation of colonies within the culture that may not be of the same origin or the same type. One advantage that stems from individual colony data is that it is possible in some instances to use an "impure" culture. Because data is collected from individual microscopic colonies there is a reduced need to separate different type colonies as is the case with macroscopic methods on solid media where it is likely that a variety of organisms would be aggregated into a macroscopic impure mass, or in a liquid suspension where it is difficult to distinguish the growth of one organism from another. Applying a growth-altering agent to a macroscopic impure mass would likely yield limited information because the effects of the growth-altering agent on the various different organisms would not be separable. Cultures made from urine or cerebrospinal samples are examples of possibly impure cultures where the present method may be used to evaluate different constituent organisms without first separating them.

Another advantage that stems from individual colony data is that it is possible to statistically analyze data pertaining to the effects of a growth-altering agent. Statistical data can be useful, for example, in determining an organism's resistance to an antibiotic. Information pertaining to the organism's antibiotic resistance can, in turn, provide valuable information regarding the optimum length of treatment. If, for example, an organism is found to be resistant to all but high concentrations of an antibiotic and the mechanism of susceptibility requires several generations to become effective, antibiotic treatment would be required for a longer period than in the case of a more sensitive organism which is immediately affected by the antibiotic.

Individual colony data also advantageously permits the identification of organism mutations that are uncharacteristically affected by the growth-altering substances. For example, the growth rates of the individual colonies can be statistically compared. If the range of growth rates exceeds the expected standard deviation of the control, it suggests that the organisms are more resistant than usual, and that resistance may be developing. It is important to emphasize that any microbial therapy must be directed to that of the most resistant organisms within the group, since these organisms will multiply even after the more sensitive organisms have been eliminated.

Another advantage of the present method is that it readily provides accurate growth-altering agent sensitivity information. A disadvantage of the Kirby-Bauer test is that there are a number of variables that affect the antibiotic concentration at any given point in the growth medium. Formulae have been published for calculating antibiotic concentrations based upon the clear zone size, but these formulae are rarely used and are considered to be approximations at best. One of the variables that can affect antibiotic concentration determination in a Kirby-Bauer is competition between adjacent organisms. In a standard plate test the organisms are in competition for food and therefore might experience inhibited growth as a result of the competition rather than as a result of the growth-altering agent. The organisms can also affect each other by their excretions and metabolic by-products. The present method avoids these types of interference by investigating the colonies shortly after inoculation, rather than waiting until the organisms have proliferated to the extent they can be seen by the naked eye.

Another advantage of the present method is its versatility. For example, the present method is capable of collecting data regarding the effect of a growth-altering agent on an organism from the moment the organism is applied to the growth medium. The present method is therefore not limited to looking at the first few generations of microbes, or only later generations that can be seen by the naked eye, but rather can be used for throughout the development of the organism. Another example of the versatility of the present method is that it can be used to investigate a particular concentration of growth-altering agent, or a gradient of concentrations of a growth-altering agent in a single test. The gradient approach avoids having to create multiple dilutions of an antibiotic, for example, to determine the minimum inhibitory concentration of that antibiotic for a particular organism. Still another example of the versatility of the present method is its ability to be used in the veterinary sciences.

The present method can also be used to facilitate the identification of particular organisms. For example, if the control reference in a particular test is a growth medium that does not contain a sugar, and the test area of the growth medium contains sugar, those organisms that can metabolize sugar will grow more rapidly in the test area than in the control area. One can therefore use a number of different growth-enhancing and growth-retarding substances to identify the organism in question.

Another advantage of the present method is its ability to provide information on effects, reactions, or lack of reactions that occur in statistically small numbers, but can nevertheless have significant implications vis-á-vis the effectiveness of the growth-altering agent on the microorganism. The advantage stems from the fact that the present method evaluates microcolonies rather than macroscopic colonies. The number of microcolonies in a given area on a growth medium will be far greater than the number of macroscopic colonies in the same area, thereby providing a statistically more significant population for evaluation in that area. For example, it is well known that some bacteria have a low mutation rate, wherein anywhere from 1 in $10^4$ to 1 in $10^6$ could be resistant particular antibiotic under certain circumstances. If the growth of this resistant strain(s) is not detected, the strain will likely be falsely reported as susceptible to the antibiotic, when in fact the strain is resistant. The advantage provided by the present is perhaps best illustrated by example. If one were to use a video camera to image macroscopic colonies on a conventional agar plate (as is presently done with some instruments used to count colonies), there is not enough room on the agar plate to contain number of non-confluent macroscopic colonies statistically necessary to have an occurrence of the above described resistant bacteria. For example, a ten (10) centimeter diameter plate plated with macroscopic colonies spaced every two (2) millimeters can only hold about 2000 such colonies, which is clearly a statistically insufficient population for detection of such mutations. This statistically insufficient population is another reason why conventional agar plates used for antibiotic susceptibility are heavily plated so as to cause confluent growth. In contrast, under the present method the CFU's that are incubated to become microcolonies can be seeded as close as ten microns ($10\mu$) apart, which allows for the evaluation of a statistically adequate $10^4$ microcolonies per square centimeter while allowing the evaluation to be performed prior to the microcolonies become confluent with one another.

Another advantage of the present method is that it can also be used to detect the presence of growth-altering agents. For example, there is utility in determining the presence of antibiotics or other growth-altering agents within a sample of milk. Current milk testing procedures require that the type of antibiotic being tested for be known up-front; i.e., the tests are tailored to particular antibiotics. Under the present method, milk is incorporated into a growth medium and an inoculum is inoculated into the growth medium. The inoculum is selected as one that is likely to be affected by the presence of a growth-altering agent (e.g., antibiotic residue) within the milk. If the growth of microcolonies originating from the inoculum is different from normal growth under the conditions at hand, then the presence of antibiotics known or unknown is likely within the sample of milk.

These and other objects, features and advantages of the present invention will become apparent in light of the detailed description of the best mode embodiment thereof, as illustrated in the accompanying drawings.

BRIEF DESCRIPTION OF THE DRAWINGS

FIGS. 1A and 1C contain unprocessed images and FIGS. 1B and 1D are the identical images of FIGS. 1A and 1C where the images were digitally processed to locate the colonies prior to quantifying their characteristics.

FIGS. 2A and 2B were taken immediately after plating and FIGS. 2C and 2D were taken after approximately two hours of incubation.

FIGS. 3A and 3B were taken immediately after plating and FIGS. 3C and 3D were taken after approximately two hours of incubation.

FIGS. 4A and 4B were taken immediately after plating and FIGS. 4C and 4D were taken after approximately two hours of incubation.

DETAILED DESCRIPTION OF THE INVENTION

Figure 1A:
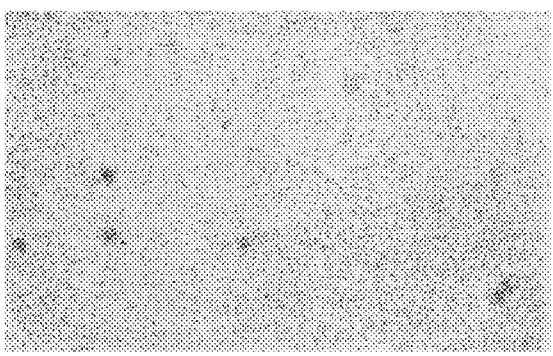
FIGS. 1A–1D contain images of a solid medium plated with *enterobacter aerogenes*.

The present method for determining the effects of a growth-altering agent on a microcolony utilizes one or more growth media capable of supporting microbial colony growth, preferably in gel, semi-solid, or permeable-solid form. Dehydrated growth media that may be rehydrated during use are particularly favorable because they can be readily stored for extended periods of time. Growth media that is clear or only moderately translucent after inoculation is also preferable because it facilitates the steps of quantifying and evaluating described below. Microcolonies can be quantified and evaluated with any growth medium, however, if proper illumination is used as will be discussed below. One or more growth media can be used to suit the application at hand.

The term "growth-altering agent" can be any chemical or environmental agent that will alter, inhibit, or enhance microbial growth. Chemical growth-altering agents include, but are not limited to, antibiotics, antiseptics, nutrients, and growth promoting agents. Environmental type growth-altering agents include, but are not limited to, parameters such as temperature, humidity, light, and gaseous environments. Chemical type growth-altering agents can be incorporated into the growth medium in a variety of ways. In those instances where it is desirable to incorporate the growth-altering agent in only a portion of the growth medium, the growth-altering agent can be incorporated using a gel or other solid or semi-solid carrier deposited on a selected portion of the growth media. In other instances, the growth-altering agent can be incorporated using a liquid carrier that permeates the entire growth medium. Environmental type growth-altering agents can be incorporated by exposing the growth-medium to particular agent, e.g., maintain a pair of the growth mediums at different temperatures, different levels of humidity or light, etc.

An inoculum containing organisms from a sample of urine, cerebrospinal fluid, body cavity fluid, or other sample source such as a suspension of organisms from a previously isolated colony(ies) is used to inoculate the growth medium. Techniques for inoculating a growth medium are well known in the art and will not be discussed further. The inoculated growth medium is incubated in a manner likely to cause constituents within the inoculum to replicate into microbial colonies.

The constituents within the inoculum that replicate into microcolonies are referred to herein as colony-forming units (CFU's). A CFU may be a viable single organism cell or a clump of organism cells present within the inoculum. After the growth medium is inoculated and incubation has begun, each CFU will have doubled at least once (absent an inhibiting factor) and become a microcolony. Meaningful information can generally be produced under the present method before a CFU has doubled four to eight (4–8) times, and almost always before it has doubled twenty (20) or so times. It should be noted that the term "doubling"as used herein refers to a doubling of area or volume of a microcolony, as opposed to an individual organism and cannot, therefore, be used to determine a single organism's size. The "doubling" of a microcolony could be due to the doubling of the number of organisms or the doubling of their average size, or some combination thereof However, since the growth of a single organism is limited, especially over the period of a few generations, the "doubling" referred to herein more often reflects true reproductive growth rather than a change in the size of the organisms.

The period during which meaningful information can be produced can also be defined in terms of colony growth time or size rather than just the number of times a CFU has doubled during incubation. For example, if the organism to be evaluated is known, it is likely that information exists regarding that organism's doubling time under similar environmental conditions. In that event, time can be used as a control parameter in the determination rather than having to directly establish how many times the organism has doubled. The size of the organism and the rate at which the area or volume of the microcolony increases in some instances can provide insight into the type of organism and the effects of the growth-altering agent on the growth rate of that organism. The period during which meaningful information can be produced can also be defined in terms of progeny. Specifically, the determination can be performed before individual microcolonies (each of which represents growth from a particular progenitor) connect or become contiguous with other microcolonies grown from different progenitors. The period during which meaningful information can be produced can also be defined as the period of time before which the growth of the microcolonies causes a substantial number of the microcolonies to become confluent with one another.

Regardless of how the evaluation period is defined, the microbial colonies utilized under the present method generally cannot be seen by the unaided human eye. The present method can, therefore, be described as microscopic in contrast to prior art methods that macroscopically evaluate multiple microbial colonies contiguous with one another that are collectively large enough so as to be viewable by the naked eye.

After incubation has begun and some of the colony-forming units have become microcolonies adequate for evaluation, one or more of the microcolonies exposed to the growth-altering agent are examined and pertinent characteristics of those colonies are quantified at one or more points in time. The colony characteristics to be quantified are chosen on the basis of those that are likely to reveal the effects of the colony's exposure to the growth-altering agent. The preferred method for quantifying characteristics includes electronically imaging a portion of the growth medium containing microcolonies that have been exposed to the growth-altering agent. If the test at hand uses microcolonies on a growth medium either not exposed to a growth-altering agent or exposed to a different concentration of a growth-altering agent as a control reference, then a portion of the control reference growth medium is electronically imaged as well.

A variety of equipment can be used to electronically image the growth medium(s) and the one or more microcolonies contained thereon. A digital camera that creates an electronic image file that can be displayed using a personal computer is particularly convenient. The digital camera can be fitted on an ordinary microscope, or preferably, on an automated microscope such as that described in co-pending U.S. patent application Ser. No. 09/255,673. In instances where a microcolony is not readily identifiable relative to the growth medium, a technique that helps contrast the microbial colony relative to the growth medium can be used. Transillumination is an acceptable illuminating technique that utilizes the fact that microcolonies have a refractive index that is appreciably different than most growth mediums. Specifically, light striking a microcolony scatters differently than light striking the growth medium, consequently making the microcolony appear darker than the growth medium. Other techniques that utilize the differences in light scattering properties include narrow-angle illumination or dark-field examination. Another means of distinguishing a microcolony from a growth medium involves staining either the microcolony or the growth medium bearing the microcolony. For example, a colorant/stain (e.g., acridine orange) introduced into the growth medium that is absorbed by a microcolony will provide contrast between the two. Alternatively, contrast between the two can be provided by a "negative" stain that gives the growth medium color or fluorescence that is occluded by the growing microcolony.

The location and extent of a microcolony can also be provided by digital processing software that detects the edge of a microcolony and digitally "fills"0 the interior area of the microcolony to distinguish it from the area outside the microcolony, or vice versa. Alternative electronic imaging systems (e.g., real time continuous imaging) may also be used depending upon the nature of the test at hand.

As stated above, the present method involves quantifying a characteristic(s) of one or more microcolonies as a function of time. If it is necessary to quantify a microcolony characteristic more than once, the imaging device must be able to locate a particular position on the growth medium one or more times. Locating a particular position can be accomplished a variety of different ways. For example, the movement and position of one or both of the imaging device and the growth medium can be mechanically or electromechanically controlled. A position on the growth medium might also be locatable by the use of recognizable features located on or in close proximity to the growth medium. A plurality of non-reactive beads distributed on the growth medium in a static pattern, for example, can be used as navigation buoys on the growth medium. U.S. patent application Ser. No. 09/366,881 describes such a method. Other locating methods or mechanisms may be used alternatively.

The characteristic(s) can be quantified by inspecting, measuring, or comparing the characteristic. In some instances, for example, useful data can be collected by inspecting one or more microcolonies for edge roughness. In other instances, useful data can be collected by measuring the area of one or more microcolonies. In still other instances, useful data can be collected by comparing the areas of one or more microcolonies exposed to a growth-altering agent against other microcolonies that have not been exposed to a growth-altering agent, or that have been exposed to a different concentration of the same growth-altering agent. It is also possible to collect useful data by comparing the exposed colony to another colony subjected to a different growth-altering agent whose effects are known. More detailed examples of how colony characteristics may be quantified are given below.

The characteristic or characteristics are quantified enough times to ensure that a clinically sufficient determination can be made regarding the effects of a growth-altering agent on an organism. Under some circumstances, it may be sufficient to quantify the characteristics of a colony once. For example, in some instances the presence of a particular characteristic (e.g., growth, bizarre microcolony morphology, etc.) may be adequate to make a clinical determination. Under other circumstances, a clinically sufficient determination may require that the characteristic or characteristics be quantified a plurality of times. A clinical determination that requires a particular effect be present over a period of time, for example, would require the characteristic or characteristics be quantified periodically. An advantage in examining the microcolonies frequently is that by using this kinetic technique, it is possible to find the relevant information in the earliest period of time, thus providing rapid clinical results. Quantifying characteristics a plurality of times can also yield additional desirable information. For example, some organisms, when in the presence of some antibiotics, show a pattern of early growth, which then slows and stops or regresses as the effects of the antimicrobial take hold. In other cases, the organisms grow very slowly and then the growth accelerates as they finally break through the antimicrobial. In both cases, the pattern of resistance or the lack of it can be elucidated by examining the growth for a few generations. The mechanism of antibiotic sensitivity may also be elucidated by examining changes in microcolony shape and density. For example, those antibiotics that have a static rather than a cidal effect, can be seen by the persistence of the CFU's, whereas an antibiotic with a cidal effect will show a disappearance of the CFU's or a sudden drop in microcolony size after some growth. This distinction may be important because cidal effects are more powerful and usually require a shorter course of treatment.

Once the characteristic(s) has been quantified, it is evaluated to determine if the growth-altering agent has had an effect on the microcolonies. The criteria used to evaluate the quantified characteristic depends on the test at hand, the characteristic, and the level of specificity necessary to provide useful data. In some instances, the evaluation criteria can be simply whether or not a quantified characteristic is present. The characteristic is quantified to establish its presence, and the determination of whether the growth-altering agent had an effect is premised on presence of the characteristic; e.g., has colony growth occurred; is the edge of a microcolony rough; etc. In such cases, the quantified characteristic by itself enables the determination. In other instances, it may be preferable to evaluate the quantified characteristic in view of a control reference.

A control reference may be any source of information that provides data useful in evaluating the characteristic of the microcolony being considered. For example, if the inoculum contains a known organism, the evaluation could be performed using a control reference that provides data relating normal growth characteristics for that organism under similar environmental conditions such as clinically developed data, etc. As an example, if a given organism is known to grow at a rate of one doubling every thirty (30) minutes under the circumstances at hand and the actual doubling rate (e.g., change in colony volume or area) is less than the known rate, then the growth-altering agent is presumed to be retarding the multiplication and growth of the organisms. Alternatively, the evaluation can be performed using a control reference in the form of a section of growth medium inoculated with the same inoculum and incubated under similar conditions that is either not subjected to the growth-altering agent at all or is subjected to a different amount of growth-altering agent. The characteristics of one or more microcolonies in the control reference portion of the growth medium and the characteristics of one or more microcolonies in the growth-altering agent applied region of the growth medium are quantified and evaluated in view of one another usually by comparison.

As stated above, the present method for determining the effects of a growth-altering agent on a microcolony provides significant advantages over methods presently available. Examples of the present method in use are offered below so that a complete appreciation of the present method may be gained. The present invention is not limited to these examples, however.

EXAMPLE 1

Figure 1B:
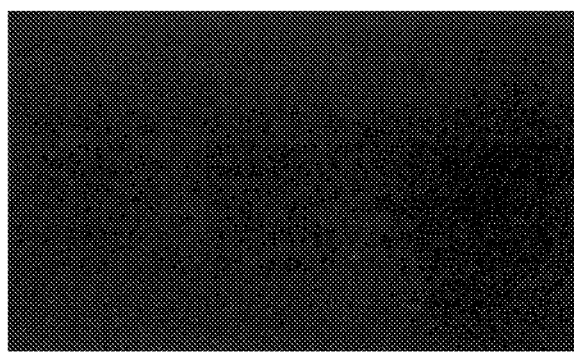
Figure 1C:
Figure 1D:
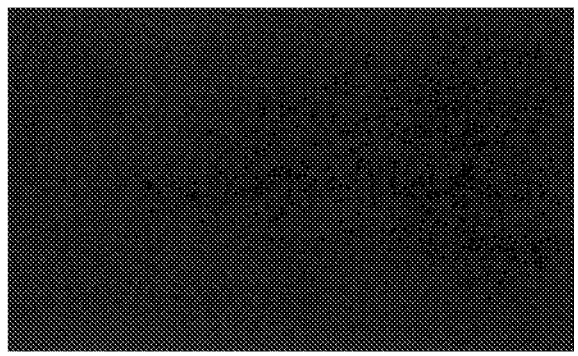

FIGS. 1A–1D contain images of a solid growth medium inoculated with *Enterobacter aerogenes*. FIG. 1A shows a region of the growth medium imaged immediately after inoculation (the time reference hereinafter referred to "$T_1$"). FIG. 1C shows the same region as FIG. 1A, but the image was taken after approximately two hours of incubation (the time reference hereinafter referred to "$T_2$"). FIG. 1B and FIG. 1D are the exact same images as FIG. 1A and FIG. 1C, respectively, except FIGS. 1B and 1D have been digitally processed to facilitate the step of quantifying the characteristics of the microcolonies. In this example, the characteristics that can be readily quantified to produce useful information are the area and shape of the microcolonies. The digital processing facilitates the process of quantifying the microcolony area and shape by detecting the edges of the microcolonies of interest and filling in those microcolonies with a contrasting color to make them more apparent. The digital processing can also be used to locate the microcolonies of interest. For example, if the area of a microcolony affects the amount of useful information it can provide, the digital processing software can be used to locate only those microcolonies having a surface area equal to or greater than a given surface area threshold. "IPLabs Spectrum" marketed by Spectrum Analytics of Vienna, Virginia, U.S.A. is an example of a software package that can be used to digitally image and quantify the microcolonies.

After the area of the microcolonies of interest are quantified, the area value of each microcolony is comparatively evaluated ($T_1$ vs. $T_2$) to determine the effects of the growth-altering agent. In some tests, it may be useful to perform multiple evaluations (i.e., at $T_1$, $T_2$, $T_3$, $T_4$, etc.). The evaluation may be performed based upon the average microcolony area, or by the distribution of microcolony areas in regions with and without the growth-altering agent. In the first instance, if the growth altering agent causes an increase (or decrease) in the growth rate, the area of the microcolonies in the region with the growth-altering agent will be greater (or lesser) than the area of the microcolonies in the control reference. In the second instance, there may be some microcolonies which grow faster (or slower) than the average, and although the average area may be the same, the distribution of colony areas will be different between the region with the growth-altering agent and the control reference. If more than two evaluations are performed, changes in growth rate can be determined by evaluating characteristics between sequential evaluation times.

To illustrate the steps of quantifying and evaluating the microcolony characteristics, and in particular microcolony growth, the growth medium shown in FIGS. 1A–1D was not exposed to a growth-altering agent. The images contained in FIGS. 1C and 1D clearly show microcolony growth. A person of skill in the art will recognize from this example that useful information can be gained in a two hour period at which time the microcolonies are only about 3–5 microns in diameter, well before they would be visible to the naked eye. As can be readily appreciated, a determination of growth and therefore the effects of a growth-altering agent can be made within this two-hour incubation period.

EXAMPLES II, III, and IV

FIGS. 2A–2D, 3A–3D, and 4A–4D show digital images of various microorganisms exposed to different growth-altering agents. Here again, the images contained in panels "A" and "B" of each FIGURE were taken immediately after inoculation, and the images contained in panels "C" and "D" of each FIGURE were taken after about two hours of incubation. None of the images in FIGS. 2A–2D, 3A–3D, and 4A–4D are enhanced by digital processing. The images contained in panels "B" and "D" of each FIGURES show regions of the growth medium that have been exposed to a growth-altering agent. The images contained in panels "A" and "C" of each FIGURE have not been exposed to a growth-altering agent and can be used as control reference areas.

a. Example II

Figure 2A:
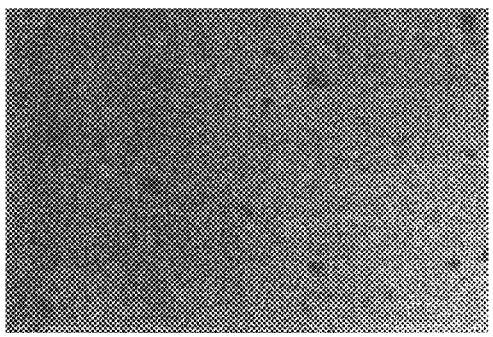
FIGS. 2A–2D contain images of *E. coli* colonies, some of which were exposed to an antibiotic.
Figure 2B:
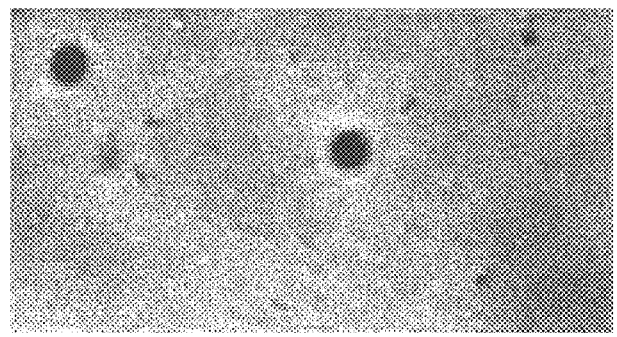
Figure 2C:
Figure 2D:
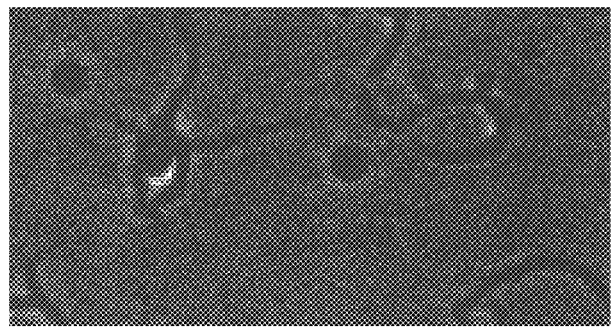

The images contained in FIGS. 2A and 2B show regions of a Kirby-Bauer type growth medium immediately after inoculation with E. coli. The images contained in FIGS. 2C and 2D show the same regions after a two-hour incubation period. The image contained in FIG. 2C shows E. coli microcolonies grown in the absence of a growth-altering agent. The image contained in FIG. 2D shows E. coli microcolonies that have been exposed to a standard clinical concentration of 2 µg/ml of the antibiotic cefotaxime. If it is desired to find the threshold of microbial sensitivity, such as is done to determine the minimum inhibitory concentration (MIC), then a series of separate regions each containing a certain concentration of the growth-altering agent may be used and the relative growth in each separate region evaluated. Alternatively, a concentration gradient of the growth-altering agent, as described in co-pending U.S. patent application Ser. No. 09/255,681 can be applied, and the microcolony growth compared over a continuum of concentrations. The microcolonies shown in FIG. 2D exhibit an increased perimeter/area ratio characteristic that suggests that the antibiotic inhibits growth by inhibiting septal formation within the microorganism colonies.

b. Example IV

Figure 3A:
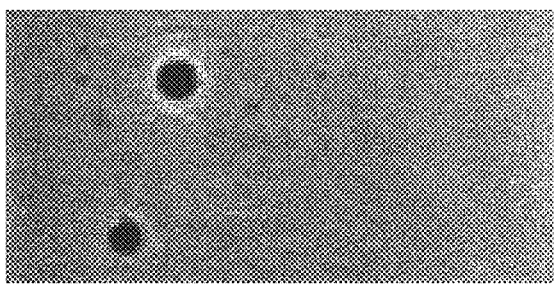
FIGS. 3A–3D contain images of *E. faecalis* some of which were exposed to an antibiotic.
Figure 3B:
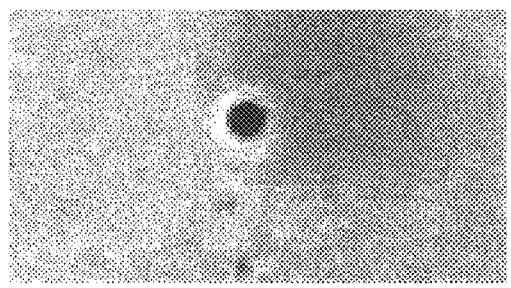
Figure 3C:
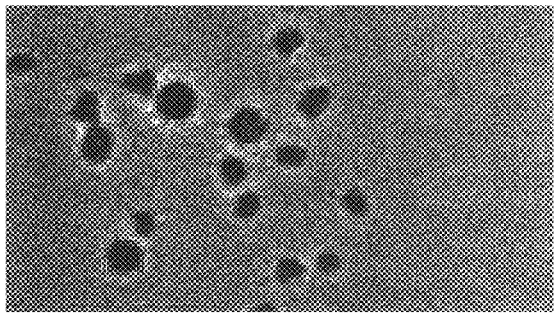
Figure 3D:
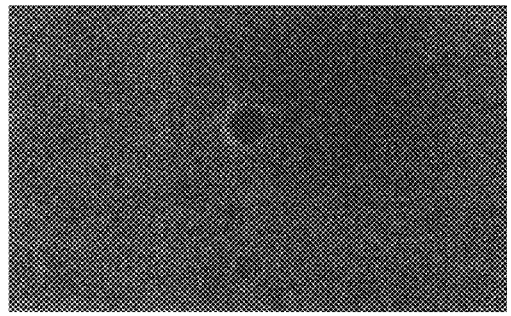

The images contained in FIGS. 3A and 3B show regions of a Kirby-Bauer type growth medium immediately after inoculation with E. faecalis. The images contained in FIGS. 3C and 3D show the same regions after a two-hour incubation period. The image contained in FIG. 3C shows E. faecalis microcolonies grown in the absence of a growth-altering agent. The image contained in FIG. 3D shows E. faecalis microcolonies that have been exposed to a standard clinical concentration of 2 µg/ml of the antibiotic vancomycin. The microcolonies shown in FIG. 2D do not appear to exhibit any growth after the two-hour period.

c. Example IV

Figure 4A:
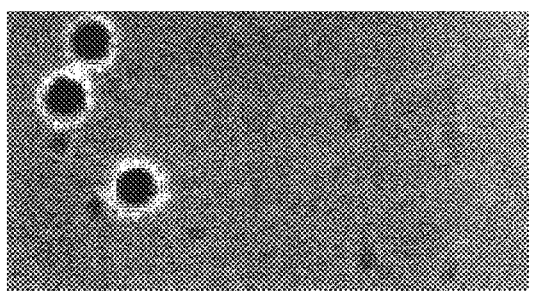
FIGS. 4A–4D contain images of *E. faecium* some of which were exposed to an antibiotic.
Figure 4B:
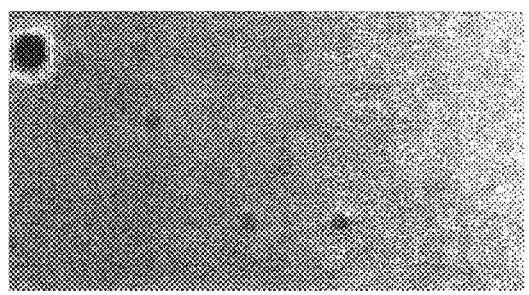
Figure 4C:
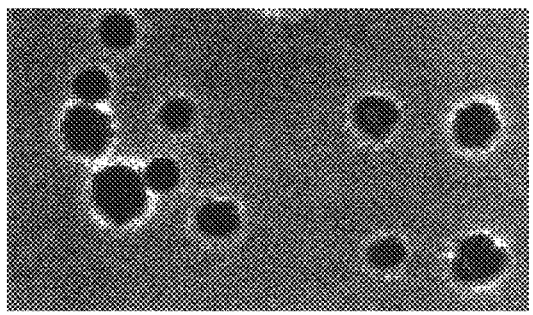
Figure 4D:
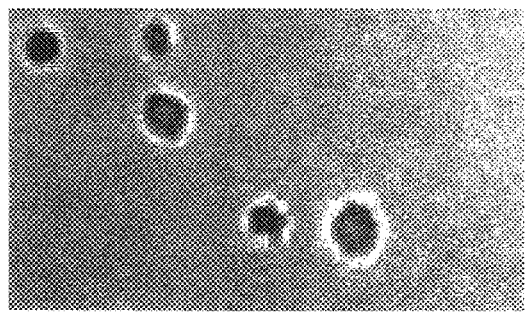

The images contained in FIGS. 4A and 4B show regions of a Kirby-Bauer type growth medium immediately after inoculation with E. faecium. The images contained in FIGS. 4C and 4D show the same regions after a two-hour incubation period. The image contained in FIG. 4C shows E. faecium microcolonies grown in the absence of a growth-altering agent. The image contained in FIG. 4D shows E. faecium microcolonies that have been exposed to a standard clinical concentration of 2 µg/ml of the antibiotic vancomycin. The microcolonies shown in FIG. 4D show detectable growth thereby indicating that the antibiotic is not an effective inhibiting agent for E. faecium in the applied concentration.

Although this invention has been shown and described with respect to the detailed embodiments thereof, it will be understood by those skilled in the art that various changes in form and detail thereof may be made without departing from the spirit and the scope of the invention. For example, the above detailed description indicates that a test area can be located in a first portion of a growth medium and a control reference can be located in a second portion of the same growth medium. Alternatively, the test area can be located in a first growth medium and the control reference in a second growth medium. Another example of a change that can be made without departing from the spirit and scope of the invention lies in the order of the steps. For example, it is preferable to incorporate the growth-altering agent into a portion or all of the growth medium prior to inoculating the growth medium with the inoculum and incubating the inoculum. It may be possible, however, to vary the order of the steps and still keep within the spirit of the present method.

What is claimed is:

1. A method for determining the effects of a growth-altering agent on one or more microbial colonies, comprising the steps of:
   providing one of a solid or a semi-solid growth medium;
   incorporating said growth-altering agent into at least a portion of said growth medium;
   inoculating said growth medium with an inoculum having one or more viable colony-forming units;
   incubating said colony-forming units in a manner likely to cause said colony-forming units to replicate into said microbial colonies;
   quantifying one or more characteristics of one or more of said microbial colonies exposed to said growth-altering agent; and
   evaluating said characteristics to determine the effects of said growth-altering agent on said microbial colonies.

2. The method of claim 1, wherein said characteristics of one or more of said microbial colonies exposed to said growth-altering agent are quantified after said colony-forming units have doubled once and before said colony-forming units have doubled more than twenty times.

3. The method of claim 2, wherein said characteristics of one or more of said microbial colonies exposed to said growth-altering agent are quantified before said colony-forming units have doubled eight times.

4. The method of claim 1 wherein said microbial colonies each have an initial area and said characteristics of said microbial colonies are quantified after at least some of said microbial colonies have increased in area two times their said initial area and before a majority of said microbial colonies have increased in area twenty times their said initial area.

5. The method of claim 1 wherein said microbial colonies each have an initial volume and said characteristics of said microbial colonies are quantified after at least some of said microbial colonies have increased in volume two times their said initial volume and before a majority of said microbial colonies have increased in area twenty times their said initial volume.

6. The method of claim 1 wherein said characteristics are quantified while each microbial colony is the product of a particular progenitor colony-forming unit.

7. A method for determining the effects of a growth-altering agent on one or more microbial colonies supported on a growth medium at least a portion of which is incorporated with said growth-altering agent, said method comprising the steps of:
   inoculating said growth medium with an inoculum containing one or more viable colony-forming units;
   incubating said colony-forming units in a manner likely to cause said colony-forming units to replicate into said microbial colonies;
   quantifying one or more characteristics of one or more said microbial colonies exposed to said growth-altering agent; and
   comparing said one or more characteristics to a control reference to determine the effects of said growth-altering agent on said microbial colonies.

8. The method of claim 7, wherein said growth-altering agent is incorporated into a first portion of said growth medium, and said control reference includes a second portion of said growth medium that is free of said growth-altering agent.

9. The method of claim 7, wherein said growth-altering agent is incorporated into a first portion of said growth medium in a first concentration, and said control reference includes a second portion of said growth medium and said growth-altering agent is incorporated into said second portion in a second concentration not equal to said first concentration.

10. The method of claim 9, wherein said second concentration is less than said first concentration.

11. The method of claim 7, wherein said growth-altering agent is applied in a gradient of concentrations, said gradient having a greater concentration end and a lesser concentration end, and wherein said control reference is located adjacent said lesser concentration end.

12. The method of claim 11, wherein said concentration of said growth-altering agent at said lesser end is ineffective on said microbial colonies.

13. The method of claim 7, wherein said control reference includes clinically developed data.

14. The method of claim 7, wherein said control reference includes one or more comparison microbial colonies having known growth characteristics.

15. The method of claim 7, wherein said control reference is located in an independent second growth medium.

16. A method for determining the effects of a growth-altering agent on one or more microbial colonies supported on a growth medium, where said growth-altering agent is incorporated into at least a portion of said growth medium, said method comprising the steps of:
   inoculating said growth medium with an inoculum having one or more viable colony-forming units;
   incubating said colony-forming units in a manner likely to cause said colony-forming units to replicate into said microbial colonies;
   periodically quantifying one or more characteristics of said one or more microbial colonies exposed to said growth-altering agent; and
   evaluating said periodic quantifications of said characteristics to determine the effects of said growth-altering agent on said microbial colonies.

17. The method of claim 16, wherein said step of periodically quantifying one or more of said microbial colonies includes periodically imaging said microbial colonies.

18. The method of claim 17, wherein said evaluating step includes comparing said periodic images to determine the effects of said growth-altering agent on said microbial colonies.

19. The method of claim 18, wherein said evaluating step includes comparing said periodic images to a control reference to determine the effects of said growth-altering agent on said microbial colonies.

20. The method of claim 19, wherein said characteristics of one or more of said microbial colonies exposed to said growth-altering agent are periodically imaged after said colony-forming units have doubled once and before said colony-forming units have doubled more than twenty times.

21. The method of claim 17, wherein said microbial colonies each have an initial area and said characteristics of said microbial colonies are periodically imaged after at least some of said microbial colonies have increased in area two times their said initial area and before a majority of said microbial colonies have increased in area twenty times their said initial area.

22. The method of claim 17, wherein said microbial colonies each have an initial volume and said characteristics of said microbial colonies are periodically imaged after at least some of said microbial colonies have increased in volume two times their said initial volume and before a majority of said microbial colonies have increased in area twenty times their said initial volume.

23. The method of claim 17, wherein said characteristics are periodically imaged while each microbial colony is the product of a particular progenitor colony-forming unit.

24. A method for determining the effects of a growth-altering agent on one or more microbial colonies supported on a growth medium at least a portion of which is incorporated with said growth-altering agent, said method comprising the steps of:
   inoculating said growth medium with an inoculum having one or more viable colony-forming units;
   incubating said colony-forming units in a manner likely to cause said colony-forming units to replicate into said microbial colonies;
   periodically imaging one or more of said microbial colonies exposed to said growth-altering agent to reveal characteristics of said microbial colonies; and
   evaluating said characteristics to determine the effects of said growth-altering agent on said microbial colonies.

25. The method of claim 24, wherein said characteristics are selected from the group consisting of microbial colony area, perimeter, perimeter-to-area ratio, edge roughness, edge contour, and uniformity of colony density.

26. A method for determining the effects of a growth-altering agent on a biological sample inoculated into a solid or semi-solid growth medium and incubated to produce microbial colonies replicated from colony-forming units present in said sample, said method comprising the steps of:
   incorporating said growth-altering agent into at least a portion of said growth medium;
   imaging said microbial colonies exposed to said growth-altering agent during a period of time when substantially all of said microbial colonies are isolated from one another; and
   evaluating characteristics of said microbial colonies to determine the effects of said growth-altering agent on said microbial colonies.

27. A method for determining the mechanism of action of a growth-altering agent on one or more microbial colonies supported on a growth medium, comprising the steps of:
   inoculating said growth medium with an inoculum having one or more viable colony-forming units;
   incorporating said growth-altering agent into at least a portion of said growth medium;
   incubating said colony-forming units in a manner likely to cause said colony-forming units to replicate into said microbial colonies;
   periodically imaging said one or more of said microbial colonies exposed to said growth-altering agent; and
   evaluating said periodic images to determine the mechanism of action of said growth-altering agent.

28. A method for determining the effects of a growth-altering agent on an organism, comprising the steps of:
   incorporating said growth-altering agent into at least a portion of a solid or semi-solid growth medium;
   inoculating said growth medium with an inoculum having one or more viable colony-forming units from said microorganism;
   incubating said colony-forming units in a manner likely to cause said colony-forming units to replicate into microcolonies of said organism;
   imaging one or more of said microcolonies exposed to said growth-altering agent a plurality of times, thereby creating chronological images of said one or more microcolonies; and
   evaluating said chronological images to determine the effects of said growth-altering agent on said organism.

29. The method of claim 28, wherein said chronological images are created after said colony-forming units have doubled once and before said colony-forming units have doubled more than twenty times.

30. The method of claim 28, wherein chronological images are created after at least some of said microcolonies have increased in area two times and before a majority of said microcolonies have increased in area twenty times.

31. The method of claim 28, wherein chronological images are created after at least some of said microcolonies have increased in volume two times and before a majority of said microcolonies have increased in volume twenty times.

32. The method of claim 28 wherein said chronological images are created while each microbial colony is the product of a particular progenitor colony-forming unit.

33. The method of claim 28, wherein characteristics of individual said microcolonies are evaluated as a test group and compared to a control group to determine if said characteristics from said test group are statistically different from characteristics of said control group.

34. The method of claim 33 where said statistical comparison is used to predict a variation in susceptibility to said growth-altering agent.

35. The method of claim 34 wherein said variation is the increasing resistance to antimicrobial agents.

36. A method for determining the effects of a growth-altering agent on one or more microbial colonies, comprising the steps of:
   providing one of a solid or a semi-solid growth medium;
   incorporating said growth-altering agent into at least a portion of said growth medium;
   inoculating said growth medium with an inoculum having a plurality of colony-forming units, wherein said colony-forming units are disposed on said growth medium spaced apart from one another a distance typically not less than $5\mu$ apart and not greater than $100\mu$ apart;
   incubating said colony-forming units in a manner likely to cause said colony-forming units to replicate into said microbial colonies;
   quantifying one or more characteristics of one or more of said microbial colonies exposed to said growth-altering agent prior to a majority of said microcolonies becoming confluent with one another; and
   evaluating said characteristics to determine the effects of said growth-altering agent on said microbial colonies.

37. A method for detecting the presence of a growth-altering agent within a sample, comprising the steps of:
   providing one of a solid or a semi-solid growth medium;
   incorporating said sample into at least a portion of said growth medium;
   inoculating said growth medium with an inoculum having one or more viable colony-forming units;
   incubating said colony-forming units in a manner likely to cause said colony-forming units to replicate into one or more microbial colonies;
   quantifying one or more characteristics of one or more of said microbial colonies exposed to said sample; and
   evaluating said characteristics to detect the presence of said growth-altering agent.

* * * * *

UNITED STATES PATENT AND TRADEMARK OFFICE
CERTIFICATE OF CORRECTION

PATENT NO.    : 6,472,166 B1
DATED         : October 29, 2002
INVENTOR(S)   : Stephen C. Wardlaw et al.

Page 1 of 1

It is certified that error appears in the above-identified patent and that said Letters Patent is hereby corrected as shown below:

<u>Column 3,</u>
Line 48, please delete "within-a given" and insert
-- within a given population will not --.

<u>Column 18,</u>
Line 39, "5µapart" should read -- 5µ apart --.
Line 40, "100µapart" should read -- 100µ apart --.

Signed and Sealed this

Twenty-fifth Day of February, 2003

JAMES E. ROGAN
*Director of the United States Patent and Trademark Office*